(12) United States Patent
Kiplinger et al.

(10) Patent No.: US 8,377,404 B2
(45) Date of Patent: Feb. 19, 2013

(54) PREPARATION OF URANIUM COMPOUNDS

(75) Inventors: Jaqueline L. Kiplinger, Los Alamos, NM (US); Marisa J. Monreal, Los Alamos, NM (US); Robert K. Thomson, Norman, OK (US); Thibault Cantat, Issy les Moulineaux (FR); Nicholas E. Travia, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/353,917

(22) Filed: Jan. 19, 2012

(65) Prior Publication Data

US 2012/0184723 A1 Jul. 19, 2012

Related U.S. Application Data

(60) Provisional application No. 61/434,284, filed on Jan. 19, 2011, provisional application No. 61/446,421, filed on Feb. 24, 2011.

(51) Int. Cl.
*C01G 43/00* (2006.01)
(52) U.S. Cl. .................................................. 423/253
(58) Field of Classification Search ................ None
See application file for complete search history.

(56) References Cited

PUBLICATIONS

Clark et al, Lewis Base Adducts of Uranium Triiodide: A New Class of Synthetically Useful Precursors for Trivalent Uranium Chemistry; Inorg. Chem., 1989, 28, 1771-1773.*

* cited by examiner

*Primary Examiner* — Paul Dickinson
(74) *Attorney, Agent, or Firm* — Samuel L. Borkowsky; Julie A. Jones

(57) ABSTRACT

$UI_3(1,4\text{-dioxane})_{1.5}$ and $UI_4(1,4\text{-dioxane})_2$, were synthesized in high yield by reacting turnings of elemental uranium with iodine dissolved in 1,4-dioxane under mild conditions. These molecular compounds of uranium are thermally stable and excellent precursor materials for synthesizing other molecular compounds of uranium including alkoxide, amide, organometallic, and halide compounds.

5 Claims, 4 Drawing Sheets

US 8,377,404 B2

PREPARATION OF URANIUM COMPOUNDS

RELATED APPLICATIONS

This application claims the benefit of copending U.S. Provisional Patent Application 61/434,284 filed Jan. 19, 2011 entitled "$UI_4$(1,4-dioxane)$_2$, [$UCl_4$(1,4-dioxane)]$_2$ and $UI_3$(1,4-dioxane)$_{1.5}$: Stable and Versatile Starting Materials for Low- and High-Valent Uranium Chemistry, and copending U.S. Provisional Application 61/446,421 filed Feb. 24, 2011 entitled "$UI_4$(1,4-dioxane)$_2$, [$UCl_4$(1,4-dioxane)]$_2$ and $UI_3$(1,4-dioxane)$_{1.5}$: Stable and Versatile Starting Materials for Low- and High-Valent Uranium Chemistry," both hereby incorporated by reference herein.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The invention relates to the preparation of molecular compounds of uranium.

BACKGROUND OF THE INVENTION

Molecular compounds of uranium are used for understanding the behavior and properties of light actinides for environmental and aqueous processing, materials for nuclear fuel cycles, and for other applications [1, 2]. Simple, safe, and inexpensive access to molecular compounds of uranium is important for developing molecular uranium chemistry.

Uranium tetrachloride ($UCl_4$) and the tetrahydrofuran (THF) adduct of uranium triiodide $UI_3$(THF)$_4$ are the currently most popular starting materials for synthesizing molecular compounds of uranium(IV) and uranium(III) [3-10]. Problems associated with synthesizing these starting materials have prompted efforts to find suitable replacements. $UI_3$ has been suggested as a suitable replacement for $UI_3$(THF)$_4$, but harsh conditions and special equipment are needed to prepare $UI_3$ [11-15].

Lewis base adducts of $UI_4$ have been reported as having limited thermal stability or as being incompatible with strong nucleophiles [16-20]. $UI_4$(diethyl ether)$_2$ [21-22] could be a replacement for $UI_4$, but the preparation of $UI_4$(diethyl ether)$_2$ is complicated and requires special equipment.

SUMMARY OF THE INVENTION

The present invention provides for a composition selected from $UI_4$(1,4-dioxane)$_2$, [$UCl_4$(1,4-dioxane)]$_2$, and $UI_3$(1,4-dioxane)$_{1.5}$.

The present invention also provides for a process for synthesizing $UI_x$(1,4-dioxane)$_y$ Wherein x is 3 and y is 1.5, or wherein x is 4 and y is 2. An embodiment of the process includes reacting a suitable amount of elemental uranium with a suitable amount of iodine ($I_2$) dissolved in 1,4-dioxane to form a suspension comprising a solid, isolating the solid from the suspension, and drying the solid under reduced pressure, thereby synthesizing $UI_x$(1,4-dioxane)$_y$.

The present invention also provides for a process for synthesizing a molecular compound of uranium. The process includes providing a solution of $UI_x$(1,4-dioxane)$_y$ wherein x is 3 and y is 1.5, or wherein x is 4 and y is 2, and reacting the solution of $UI_x$(1,4-dioxane)$_y$ under suitable conditions to form the molecular compound of uranium.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
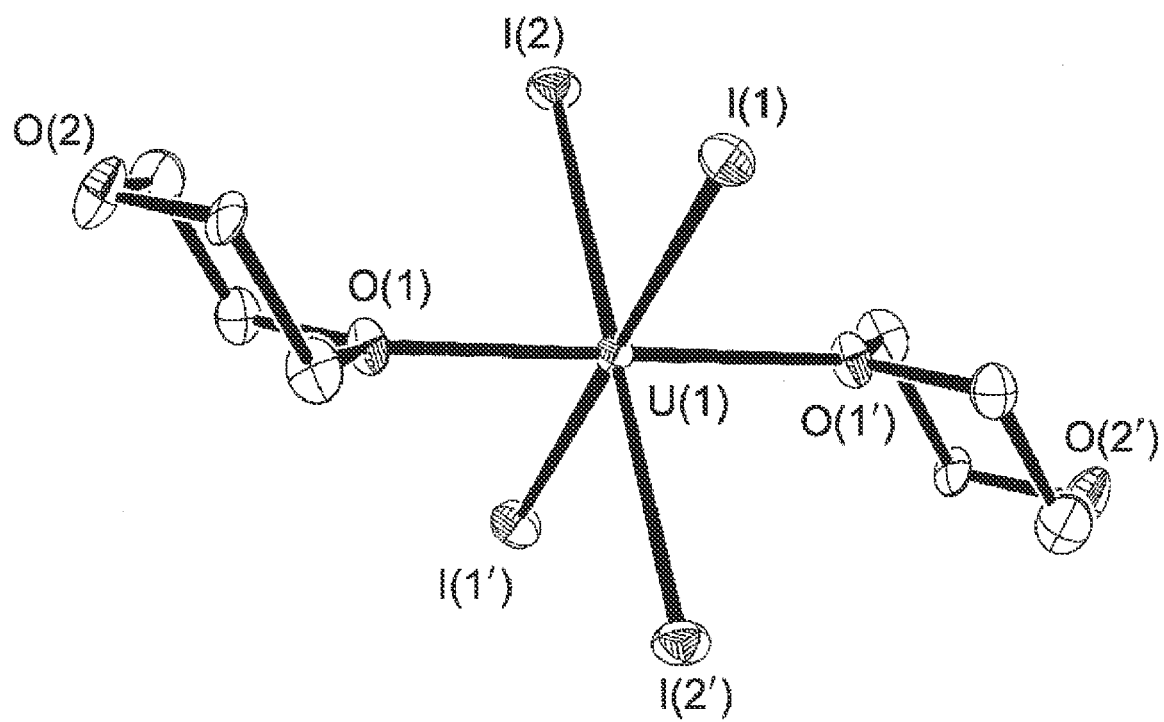
FIG. 1 shows the molecular structure of $UI_4$(1,4-dioxane)$_2$.

This invention relates to the preparation of molecular compounds of uranium. An aspect of this invention relates to molecular compounds of uranium that are themselves precursor materials used to prepare other molecular compounds of uranium.

The terms "complex" and "molecular compound" are used interchangeably herein. Complexes of uranium are materials that typically include a uranium center and various ligands that are bound to the uranium center. A dimer includes two uranium centers and various ligands bound to the uranium centers. The uranium center for the complexes described herein is most likely a uranium(III) or a uranium(IV) center. Aspects of the present invention are described by Marisa J. Monreal, Robert K. Thomson, Thibault Cantat, Nicholas E. Travia, Brian L. Scott, and Jaqueline L. Kiplinger in Organometallics 2011, vol. 30, pp 2031-2038, incorporated herein by reference in its entirety.

The precursor materials include a uranium(III) or a uranium(IV) center, 1,4-dioxane ligands, and halide ligands. Preferred halide ligands are iodide and chloride. The precursor materials are synthesized under mild conditions without the use of any specialized equipment. The precursor materials are thermally stable and can be used to synthesize other molecular compounds of uranium.

ThCl$_4$(1,4-dioxane)$_2$, has been prepared under mild conditions from ThCl$_4$(H$_2$O)$_4$, trimethylsilylehloride (Me$_3$SiCl), hydrochloric acid (HCl), and the donor ligand 1,4-dioxane [23]. ThCl$_4$(1,4-dioxane) has been converted to other compounds by replacing the 1,4-dioxane ligands with stronger donor ligands such as 1,2-dimethoxyethane (DME) and tetrahydrofuran (THF). The present invention relates to 1,4-dioxane adducts of molecular compounds of uranium that are themselves precursors for other molecular compounds of uranium.

An embodiment of the present invention is the molecular compound UI$_4$(1,4-dioxane)$_2$. It has a uranium(IV) metal center, four iodide ligands, and 2 ligands of 1,4-dioxane. This compound was synthesized by reacting turnings of elemental uranium with 2.05 equivalents of molecular iodine (I$_2$) in 1,4-dioxane solvent at room temperature for 7 days. It is a red-orange solid and was isolated in 95% yield. The rate of reaction may be increased by increasing the reaction temperature. When the reaction temperature was raised to 50° C., for example, the reaction time was shortened to 18 hours. The synthesis of UI$_4$(1,4-dioxane)$_2$ can be perforated easily on multi-gram and larger scales. The process does not require prior purification of iodine by sublimation, activation of the uranium turnings by sonication, or by using HgI$_2$ as an activator.

UI$_4$(1,4-dioxane)$_2$ was characterized by $^1$H NMR spectroscopy, X-ray crystallography, and elemental analysis. The $^1$H NMR spectrum of UI$_4$(1,4-dioxane)$_2$ at ambient temperature in C$_6$D$_6$ solvent exhibits a broad singlet at 132 ppm. The broadness of the singlet peak suggests that the 1,4-dioxane ligand coordinates reversibly in solution at room temperature to the uranium metal center.

An X-ray crystal structure of UI$_4$(1,4-dioxane)$_2$ was determined from dark-red crystals grown from a toluene:1,4-dioxane (90:10) solution at –30° C. FIG. 1 shows the molecular structure of UI$_4$(1,4-dioxane)$_2$. Thermal ellipsoids were projected at the 50% probability level. Hydrogen atoms were omitted for clarity. As FIG. 1 shows, UI$_4$(1,4-dioxane)$_2$ has octahedral symmetry with trans-bound 1,4-dioxane ligands and four equatorial iodide ligands. There is an inversion center at the uranium metal center and no deviation of the iodide ligands from the equatorial plane. Selected bond distances (Å) and angles (°): U(1)-I(1)=2.9637(11); U(1)-I(2)=2.9588 (10); U(1)-O(1)=2.333(6); I(1)-U(1)-I(2)=90.31(3); I(1)-U(1)-O(1)=89.53(15); I(2)-U(1)-O(1)=89.74(16); O(1)-U(1)-O(1')=179.999(1). The U—I bond distances of 2.9637(11) and 2.9588(10) are on the short end of the range observed for a handful of structurally characterized Lewis base adducts of UI$_4$ (for example, UI$_4$(N≡CPh)$_4$, U—I=3.027(1) Å [20]; UI$_4$(py)$_3$, U—I=2.9558(4)-3.0438(4) Å [19]; UI$_4$(O═C (NMe$_2$)$_2$]$_4$, U—I=2.996(3), 3.027(3) Å [16]; UI$_4$(diethyl ether)$_2$, U—I=2.9614(6) Å [21]. The U—I bond distance for UI$_4$(1,4-dioxane)$_2$ may be due to the weaker donor strength of 1,4-dioxane. Consistent with a weaker donor strength of 1,4-dioxane, the U—O bond length of 2.333(6) Å is comparable to those observed for the diethyl ether complexes UI$_4$(diethyl ether)$_2$ (2.366(8) Å [21]) and longer than those reported for the N,N,N',N'-tetramethylurea complex UI$_4$[O═C(NMe$_2$)]$_4$ (2.20(3), 2.17(3) Å [16]).

UI$_4$(1,4-dioxane)$_2$ is more thermally stable compared to either UI$_4$(THF)$_4$ or UI$_4$(diethyl ether)$_2$. UI$_4$(THF)$_4$ is too thermally unstable to be isolated [18, 24]; it can be generated in-situ at room temperature from UI$_4$(N≡CMe)$_4$ in THF solvent but undergoes a rapid ring-opening of THF [18]. UI$_4$(diethyl ether)$_2$ is also thermally unstable, and loses diethyl ether above room temperature [21, 22, 25]. UI$_4$(diethyl ether)$_2$ also reacts with glass surfaces to yield [H(diethyl ether)$_2$][UI$_5$(diethyl ether)] [25]. By contrast, UI$_4$(1,4-dioxane)$_2$ is stable in 1,4-dioxane or toluene solvent for 12 hours at 80° C. without degradation and can be stored at room temperature under an inert atmosphere for at least two weeks. This greater stability may be due to the higher boiling point of 1,4-dioxane, which limits loss of the 1,4-dioxane ligand [26], and also may be due to a lower susceptibility of coordinated 1,4-dioxane toward metal mediated nucleophilic attack.

Figure 2:
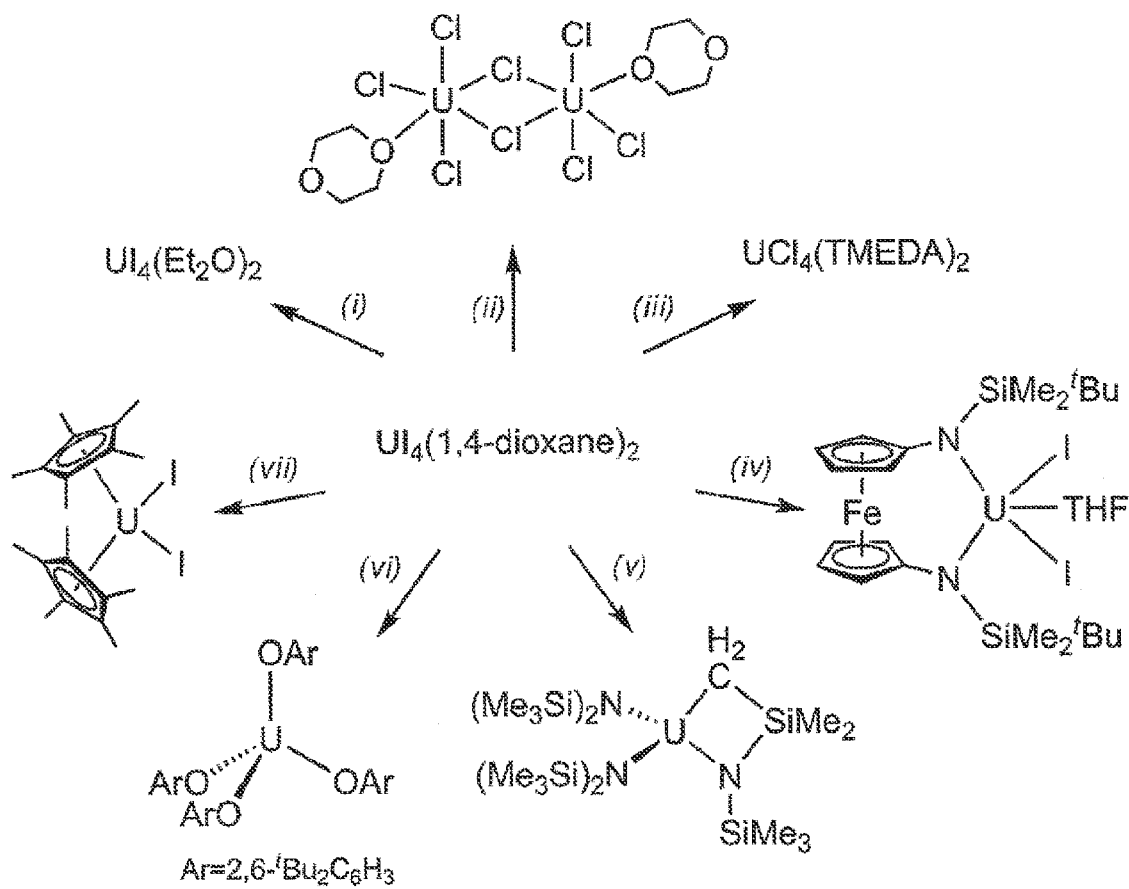
FIG. 2 shows the synthesis of molecular compounds of uranium using $UI_4$(1,4-dioxane)$_2$ as a precursor material. The reagents and conditions for reactions i, ii, iii, iv, v, vi, and vii are: (i) diethyl ether ($Et_2O$), room temperature (rt), 1 hour (h), 71% yield; (ii) 4 equivalents (equiv) anhydrous hydrochloric acid (NCl, 4.0 M/1,4-dioxane), 1,4-dioxane, room temperature, 10 minutes (min), 86% yield; (iii) (1) 2.2 equiv TMEDA, (N,N'-tetramethylethylenediamine), toluene, rt, 18 h; (2) 5 equiv HCl (4.0 M/1,4-dioxane), rt, 4 h; (3) 5 equiv TMEDA, rt, 1 h, 91% yield; (iv) [$K_2$(OEt$_2$)$_2$]fc[NSi($^t$Bu)Me$_2$]$_2$, THF, −35° C.→rt, 1 h, 61% yield; (v) 4 equiv K[N(SiMe$_3$)$_2$], toluene, 110° C., 15 h, 70% yield; (vi) 4.1 equiv K(O-2,6-$^t$Bu$_2$C$_6$H$_3$), THF, rt, 12 h, 64% yield; (vii) 2 equiv K(C$_5$Me$_5$), toluene, 110° C., 18 h, 65% yield.

UI$_4$(1,4-dioxane)$_2$ is an excellent precursor material for synthesizing molecular compounds of uranium(IV). FIG. 2 shows some examples of the reaction chemistry. According to FIG. 2, UI$_4$(1,4-dioxane)$_2$ reacts with diethyl ether at room temperature (i.e. (i)) to yield UI$_4$(diethyl ether)$_2$ in 71% isolated yield [21]. UI$_4$(1,4-dioxane)$_2$ reacts with anhydrous HCl (4.0 M/1,4-dioxane) to yield the chloride-bridged dimer complex [UCl$_4$(1,4-dioxane)]$_2$, which precipitates from the reaction mixture. A simple workup produced the dimer in 86% isolated yield. UI$_4$(1,4-dioxane)$_2$ reacts first with N,N'-tetramethylethylenediamine (TMEDA) and then with anhydrous HCl (4.0M/1,4-dioxane) to yield the known molecular compound UCl$_4$(TMEDA)$_2$ [27] in 91% yield. Salt metathesis chemistry provides access to amide, alkoxide and organometallic compounds as illustrated by the synthesis of (iv) fc[NSi($^t$Bu)Me$_2$]$_2$UI$_2$(THF) [28], (v) [(Me$_3$Si)$_2$N]$_2$U[κ$^2$-(C, N)—CH$_2$Si(Me)$_2$N(SiMe$_3$)] [29, 30], (vi) U(O-2,6-$^t$Bu$_2$C$_6$H$_3$)$_4$ [31-33], and (vii) (C$_5$Me$_5$)$_2$UI$_2$ [34-36]. As FIG. 2 shows, UI$_4$(1,4-dioxane)$_2$ provides an efficient and atom-economical way to access uranium(IV) iodide compounds. UI$_4$(1,4-dioxane)$_2$ reacts with [K$_2$(OEt$_2$)$_2$]fc[NSi ($^t$Bu)Me$_2$]$_2$ to produce fc[NSi($^t$Bu)Me$_2$]$_2$UI$_2$(THF) in 1 hour. UI$_4$(1,4-dioxane)$_2$ easily reacts with 2 equivalents of K(C$_5$Me$_5$) to afford (C$_5$Me$_5$)$_2$UI$_2$ in 65% isolated yield.

Figure 3:
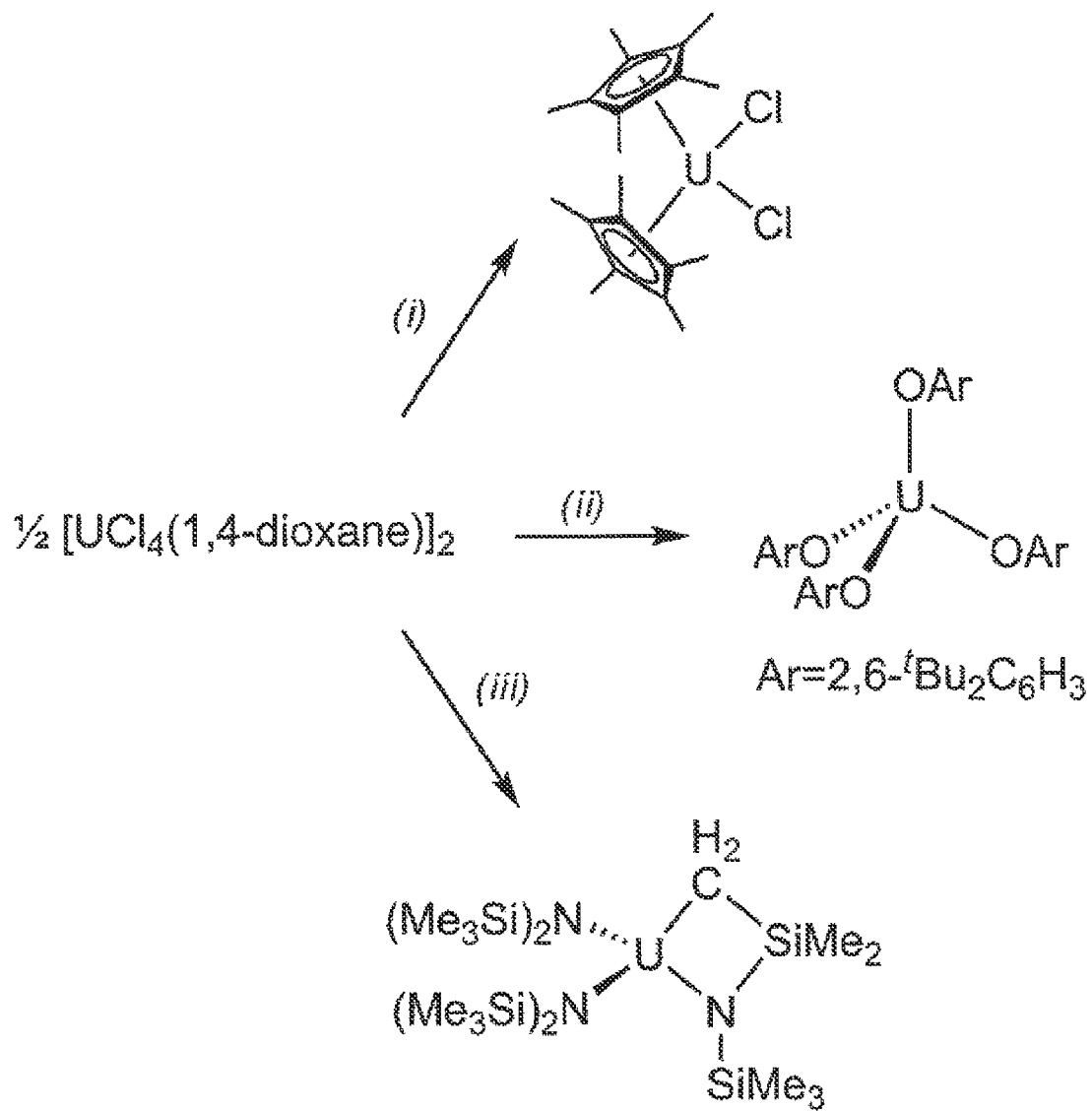
FIG. 3 shows the synthesis of molecular compounds of uranium using the dimer [$UCl_4$(1,4-dioxane)]$_2$ as a precursor material. Reagents and conditions for reactions i, ii, and iii are: (i) 2 equiv (C$_5$Me$_5$)MgCl(THF), toluene, 110° C., 15 h, 70% yield; (ii) 4.3 equiv K(O-2,6-$^t$Bu$_2$C$_6$H$_3$), toluene, 70° C., 15 h, 65% yield; (iii) 4 equiv Na[N(SiMe$_3$)$_2$], toluene, 110° C., 15 h, 80% yield.

[UCl$_4$(1,4-dioxane)]$_2$ is an excellent precursor for various molecular compounds of uranium, and its safe, high-yielding, room temperature synthesis represents a considerable advance over the existing preparative routes to UCl$_4$. FIG. 3 shows some of the reaction chemistry for [UCl$_4$(1,4-dioxane)]$_2$. [UCl$_4$(1,4-dioxane)]$_2$ reacts with, for example, (C$_5$Me$_5$)MgCl(THF) to give the known dichloride complex (C$_5$Me$_5$)$_2$UCl$_2$ [37]. [UCl$_4$(1,4-dioxane)]$_2$ also reacts with K[O-2,6-$^t$Bu$_2$C$_6$H$_3$] to give U(O-2,6-$^t$Bu$_2$C$_6$H$_3$)$_4$ [31, 33], or with Na[N(SiMe$_3$)$_2$] to give [(Me$_3$Si)$_2$N]$_2$U[κ$^2$-(C,N)—CH$_2$Si(Me)$_2$N(SiMe$_3$)] [29, 30].

UI$_3$(1,4-dioxane)$_{1.5}$ is an embodiment precursor complex of this invention. It was synthesized by reacting turnings of elemental uranium with 1.35 equivalents of iodine in 1,4-dioxane solvent at room temperature fir 18 hours. It was isolated in 99% yield as a robust, blue-violet solid. UI$_3$(1,4-dioxane)$_{1.5}$ was also prepared at a higher temperature (80° C.) in comparable yields. UI$_3$(1,4-dioxane)$_{1.5}$ can be synthesized on multi-gram scales and higher, and the synthesis does not require the pre-purification of iodine by sublimation or the activation of the uranium turnings by sonication or with a HgI$_2$ activator. The UI$_3$(1,4-dioxane)$_{1.5}$ does not suffer the problems associated with UI$_3$(THF)$_4$ [3, 4] that are related to decomposition of the intermediate UI$_4$(THF)$_4$ by ring-opening of coordinated THF at room temperature [4, 19]. The analogous synthesis in diethyl ether affords the adduct-free complex UI$_3$ [21], which demonstrates the relative higher donor strength of 1,4-dioxane compared to diethyl ether towards uranium(III); the 1,4-dioxane ligands in UI$_3$(1,4-dioxane)$_{1.5}$ are not displaced by diethyl ether.

The synthesis of UI$_3$(1,4-dioxane)$_{1.5}$ initially involves the generation of UI$_4$(1,4-dioxane)$_2$ which appears as a red intermediate within a few hours and is later reduced to blue-violet $UI_3(1,4\text{-dioxane})_{1.5}$. This was confirmed by the reaction of $UI_4(1,4\text{-dioxane})_2$ with uranium turnings in 1,4-dioxane at room temperature, which quantitatively gives $UI_3(1,4\text{-dioxane})_{1.5}$. $UI_3(1,4\text{-dioxane})_{1.5}$ is only slightly soluble in 1,4-dioxane and is insoluble in diethyl ether and non-coordinating solvents such as benzene, toluene or hexane. The identity of the complex was established by H, C, I and U elemental analyses, ligand displacement by other coordinating solvents (THF or pyridine), and reaction chemistry. The poor solubility of $UI_3(1,4\text{-dioxane})_{1.5}$ may be due to self-polymerization to a form a polymeric extended structure with bridging 1,4-dioxane ligands [23].

Figure 4:
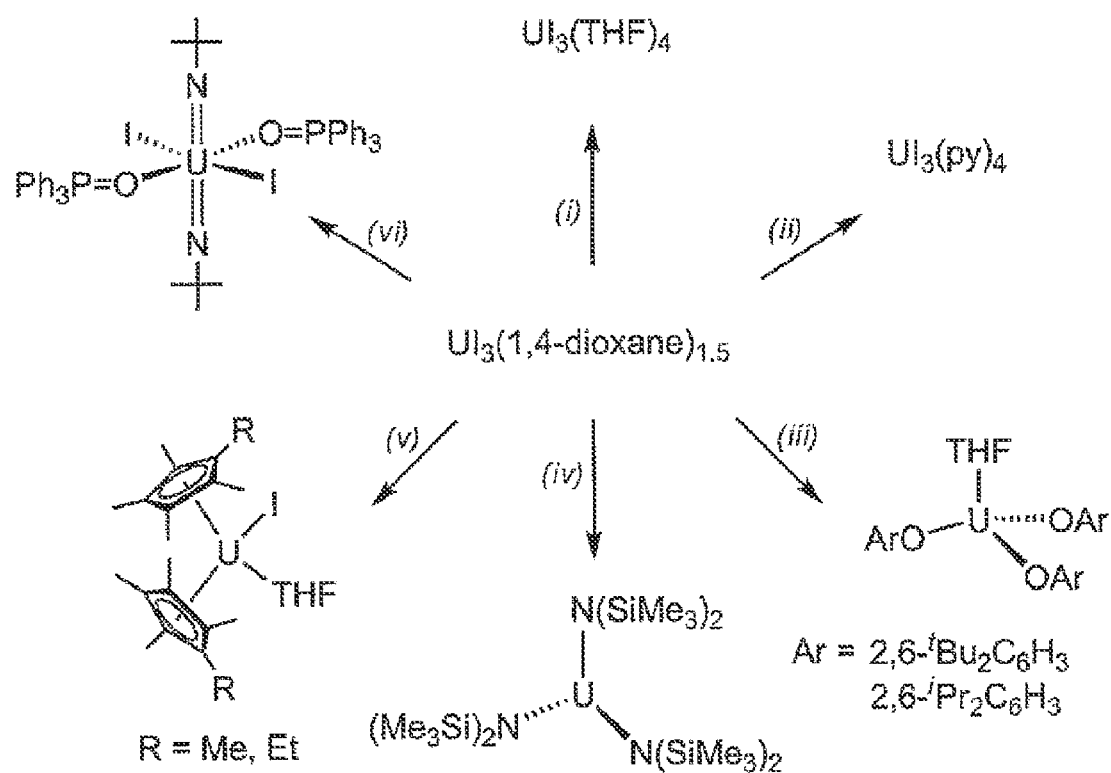
FIG. 4 shows the synthesis of molecular compounds of uranium using $UI_3$(1,4-dioxane)$_{1.5}$ as a precursor material. Reagents and conditions for reactions i, ii, iii, iv, v, vi, are: (i) THF, rt, 1 h, 98% yield; (ii) pyridine, rt, 4 h, 89% yield; (iii) 3 equiv KOAr (Ar=2,6-$^t$Bu$_2$C$_6$H$_3$, 2,6-$^t$Pr$_2$C$_6$H$_3$), THF, rt, 1 h, 81-82% yield; (iv) 3 equiv Na[N(SiMe$_3$)$_2$], THF, rt, 1 h, 73% yield; (v) 2 equiv K(C$_5$Me$_4$R) (R=Me, Et), THF, rt, 18 h, 67-75% yield; (vi) (1) 6.8 equiv $^t$BuNH$_2$, 1.5 equiv $I_2$, THF, rt, 10 min; (2) 2.3 equiv Ph$_3$P=O, rt, 15 h, 46% yield.

$UI_3(1,4\text{-dioxane})_{1.5}$ is a versatile precursor for synthesizing molecular compounds of uranium. Some examples are summarized in FIG. 4. The 1,4-dioxane ligands in $UI_3(1,4\text{-dioxane})_{1.5}$ are displaced by strong donor ligands such as THF and pyridine to form the known complexes $UI_3(THF)_4$ [3] and $UI_3(py)_4$ [4]. The bidentate ligand DME did not displace the coordinated 1,4-dioxane from $UI_3(1,4\text{-dioxane})_{1.5}$ to form the known adduct $UI_3(DME)_2$, even when heated to 75° C. for 2 hours. The aryloxide and homoleptic amide complexes $U(OAr)_3(THF)$ ($Ar=2,6\text{-}^tBu_2C_6H_3$ [38], $2,6\text{-}^iPr_2C_6H_3$ [39], and $U[N(SiMe_3)_2]_3$ [3, 4, 21, 40, 41] were obtained in good yields by salt metathesis using 3 equiv K(OAr) and $Na[N(SiMe_3)_2]$, respectively. The mono-iodide complexes $(C_5Me_4R)_2UI(THF)$ (R=Me [48] and Et [43] were synthesized in high yield by reacting $UI_3(1,4\text{-dioxane})_{1.5}$ with 2 equiv $K(C_5Me_4R)$ (R=Me, Et). Reaction of $UI_3(1,4\text{-dioxane})_{1.5}$ with tert-butylamine and iodine in THF, followed by $Ph_3P=O$ in toluene, gave the linear bis(imido) uranium(VI) complex shown in FIG. 4 in 46% isolated yield [44]. This shows that the reactivity of $UI_3(1,4\text{-dioxane})_{1.5}$ is not limited to the preparation of trivalent uranium.

Unless otherwise noted, all reactions and manipulations were performed at 20° C. in a recirculating VACUUM ATMOSPHERES NEXUS Model inert atmosphere ($N_2$) drybox equipped with a 40 CFM Dual Purifier NI-Train. Glassware was dried overnight at 150° C. before use. All NMR spectra were obtained using a BRUKER AVANCE 300 MHz spectrometer. Chemical shifts for $^1H$ NMR spectra were referenced to solvent impurities. Elemental analyses were performed at the University of California, Berkeley Microanalytical Facility, Columbia Analytical Services (Tucson, Ariz.), or Midwest Microlab, LLC (Indianapolis, Ind.). Heating can be performed inside a ventilation hood using oil baths and thick-walled Schlenk tubes equipped with Teflon valves. However, it was more convenient to heat reactions inside the glovebox using an IKA RCT Basic stirring hotplate equipped with an ETS-D5 thermocouple and CHEMGLASS reaction PIE-BLOCK hardware, which have a drilled thermowell for insertion of an electronic contact thermometer.

Unless otherwise noted, reagents were purchased from commercial suppliers and used without further purification. Celite (ALDRICH), alumina (BROCKMAN I, ALDRICH) and 4 Å molecular sieves (ALDRICH) were dried under dynamic vacuum at 250° C. for 48 hours prior to use. All solvents (ALDRICH) were purchased anhydrous and were dried over KH for 48 hours, passed through a column of activated alumina, and stored over activated 4 Å molecular sieves prior to use. Benzene-$d_6$ (ALDRICH), toluene-$d_8$ (ALDRICH) and tetrahydrofuran-$d_8$ (CAMBRIDGE, ISOTOPE LABORATORIES) were purified by storage over activated 4 Å molecular sieves or sodium metal prior to use. $^{238}U$ turnings were obtained from Los Alamos National Laboratory and cleaned as described below. Iodine was purchased from ALDRICH and used as received. $[K_2(OEt_2)_2]fc[NSi(^tBu)Me_2]_2$ [45] and $K(C_5Me_4Et)$ [43] were prepared according to literature procedures.

Depleted uranium (primary isotope $^{238}U$) is a weak α-emitter (4.197 MeV) with a half-life of $4.47 \times 10^9$ years. Manipulations and reactions were carried out in monitored fume hoods or in an inert atmosphere drybox in a radiation laboratory equipped with α- and β-counting equipment.

Oxide-Free Uranium Metal Turnings were prepared by a modifying a known procedure [4]. Twenty grams of oxide-coated depleted uranium turnings were immersed in 100 mL of concentrated nitric acid to remove the oxide coating. The turnings were mixed and swirled in the nitric acid. The reaction of nitric acid with uranium metal was accompanied by the evolution of heat and brown $NO_2$ gas as the metal turnings lost the black oxide coating. The nitric acid was carefully decanted from the turnings. The nitric acid washing was repeated two more times until the turnings displayed a shiny, metallic surface. Residual acid was removed by rinsing the turnings three times with copious amounts of deionized water. The resulting shiny turnings were then rinsed three times (3×100 mL) with acetone to remove water. The turnings were then transferred into the drybox antechamber where the residual acetone was removed under reduced pressure.

$K(C_5Me_5)$ was synthesized by the following procedure, which is a modified literature procedure [46] similar to that reported for $K(C_5Me_4H)$ [14] and $K(C_5Me_4Et)$ [43, 46]. A 250-mL side-arm flask equipped with a magnetic stir bar was charged with $K[N(SiMe_3)_2]$ (18.3 grams (g), 91.8 millimoles (mmol)) and 125 milliliters (mL) diethyl ether ($Et_2O$). The resulting slurry was stirred at room temperature. To this stirring suspension was added $C_5Me_5H$ (15.0 g, 110 mmol) dropwise by pipette over 10 minutes. The solution became increasingly cloudy. The resulting white suspension was stirred for 15 hours at room temperature, then filtered through a medium-porosity fritted filter to collect an off-white powder, which was washed with $Et_2O$ (20 mL) and dried under reduced pressure to give $K(C_5Me_5)$ as an off-white powder (16.0 g, 91.8 mmol, 100%; $^1H$ NMR (THF-$d_8$, 298 K): δ 1.93 (s, 15H, $C_5Me_5$).

The compounds K(OAr) wherein $Ar=2,6\text{-}^tBu_2C_6H_3$ and $2,6\text{-}^iPr_2C_6H_3$ were synthesized by the following procedure, which is a modification of a literature procedure [32, 47]. The synthesis of $K(O\text{-}2,6\text{-}^tBu_2C_6H_3)$ and $K(O\text{-}2,6\text{-}^iPr_2C_6H_3)$ are analogous, and the preparation of $K(O\text{-}2,6\text{-}^tBu_2C_6H_3)$ is given as a representative example. A 125-mL side-arm flask equipped with a magnetic stir bar was charged with 2,6-di-tert-butylphenol (2.00 g, 9.69 mmol) and THF (30 mL). To this clear, colorless, stirring solution, $K[N(SiMe_3)_2]$ (1.61 g, 8.08 mmol) was added as a solid, generating a pale yellow solution. The resulting solution was stirred at room temperature for 15 hours, after which time the volatiles were removed under reduced pressure. The resulting pale pink solid was washed with pentane (25 mL), collected by filtration through a medium-porosity fritted-filter, and dried under reduced pressure to afford $K(O\text{-}2,6\text{-}^tBu_2C_6H_3)$ as a white solid (1.96 g, 8.04 mmol, 99%; $^1H$ NMR (THF-$d_8$, 298 K): δ 6.72 (d, 2H, m-Ar—H), 5.77 (t, 1H, p-Ar—H), 1.38 (s, 18H, C—$CH_3$). $K(O\text{-}2,6\text{-}^iPr_2C_6H_3)$: $^1H$ NMR (THF-$d_8$, 298 K): δ 6.69 (d, J=7 Hz, 2H, m-Ar—H), 6.07 (t, J=7 Hz, 1H, p-Ar—H), 3.51 (sept, J=7 Hz, 2 H, $CHMe_2$), 1.12 (d, J=6 Hz, 12H, $CHMe_2$).

$UI_4(1,4\text{-dioxane})_2$ was synthesized by two procedures. The first procedure was performed at room temperature. The second procedure was performed at 50° C.

The room temperature procedure for synthesizing $UI_4(1,4\text{-dioxane})_2$ began with charging a 20-mL scintillation vial with a stir bar, uranium turnings (1.02 g, 4.28 mmol), iodine (2.23 g, 8.78 mmol), and 1,4-dioxane (10 mL). The reaction mixture was stirred vigorously for 7 days at room temperature to give a thick brick-red suspension. The reaction mixture was filtered over a medium-porosity fritted filter to collect a red-orange solid. The solid was washed with a 1:1 mixture of hexane and the non-coordinating solvent bis(trimethylsilyl) ether ($TMS_2O$, 3×15 mL) and dried under reduced pressure to give $UI_4(1,4\text{-dioxane})_2$ (1) as a red-orange solid (3.75 g, 4.06 mmol, 95%). Analysis calculated for $C_8H_{16}I_4O_4U$ (mol. wt. 921.86): C, 10.42; H, 1.75; I, 55.06; found: C, 11.08; H, 1.70; I, 50.0; $^1H$ NMR ($C_6D_6$, 298 K): δ 3.31 (broad singlet, $v_{1/2}$=69 Hz, 16H, $CH_2$).

The second procedure used for synthesizing $UI_4(1,4\text{-dioxane})$, began with charging a 50-mL round bottom flask with a large stir bar, uranium turnings (2.13 g, 8.94 mmol), iodine (4.65 g, 18.3 mmol) and 1,4-dioxane (12 mL). The reaction mixture was stirred vigorously for 18 h at 50° C., using a thermocouple-equipped IKA stirring hotplate, yielding a brick-red suspension. The reaction mixture was cooled to room temperature and filtered over a medium-porosity fritted filter to collect a red-orange solid. The solid was washed with a 1:1 mixture of hexane and the non-coordinating solvent $TMS_2O$ (3×15 mL), and dried under reduced pressure to give $UI_4(1,4\text{-dioxane})_2$ (1) as a red-orange solid (7.94 g, 8.61 mmol, 96%).

$UI_4$(diethyl ether)$_2$ was synthesized by the following procedure: A 20-mL scintillation vial was charged with a stir bar, $UI_4(1,4\text{-dioxane})_2$ (1) (0.101 g, 0.110 mmol) and diethyl ether (15 mL). The reaction mixture was stirred for 1 h at room temperature and then concentrated to approximately 3 mL. Pentane (10 mL) was added, resulting in precipitation of a red solid. The solid was collected by filtration on a medium-porosity fritted filter and dried under reduced pressure to give $UI_4$(diethyl ether)$_2$ (2) as a red solid (0.069 g, 0.078 mmol, 71%). The $^1H$ NMR spectrum collected in $C_6D_6$ was consistent with the data previously reported for $UI_4$(diethyl ether)$_2$ [21]. The $^1H$ NMR spectrum ($C_6D_6$ at 298 K) included the following peaks: δ −10.53 (s, 6H, $O(CH_2CH_3)_2$), −22.54 (s, 4H, $O(CH_2CH_3)_2$).

$[UCl_4(1,4\text{-dioxane})]_2$ was synthesized by the following procedure: A 125-mL side-arm flask was charged with a stir bar, $UI_4(1,4\text{-dioxane})_2$ (1.50 g, 1.63 mmol) and 1,4-dioxane (35 mL). HCl (4 M/1,4-dioxane, 2 mL, 8 mmol) was added to this suspension over 1 minute. Initially, the red-orange suspension clears up and turns dark red. Additional HCl causes the rapid formation of a yellow precipitate. The reaction mixture was vigorously stirred for 10 minutes at room temperature to give a yellow precipitate. The yellow solid was collected by filtration over a medium-porosity fritted filter, washed sequentially with 1,4-dioxane (5 mL) and hexane (2×15 mL), and dried thoroughly under reduced pressure. The product changed color from yellow to orange while drying, to give $[UCl_4(1,4\text{-dioxane})]_2$ as an orange solid (0.655 g, 0.700 mmol, 86%) Analysis calculated for $C_8H_{16}Cl_8O_4U_2$ (mol. wt. 935.89): C, 10.27; H, 1.72; found: C, 9.90; H, 1.39. The $^1H$ NMR spectrum ($C_6D_6$ at 298 K) included the following peak: δ 1.25 (broad singlet, 16H, $CH_2$). $[UCl_4(1,4\text{-dioxane})]_2$ has poor solubility in $C_6D_6$ and the chemical shift of the product can vary between δ 1.25 and 1.75 depending on the concentration and temperature.

$UCl_4(TMEDA)_2$ was synthesized by the following procedure: A 20-mL scintillation vial was charged with a stir bar, $UI_4(1,4\text{-dioxane})_2$ (0.194 g, 0.211 mmol) and toluene (10 mL). TMEDA (0.0538 g, 0.463 mmol) was added to the resulting solution and the reaction was stirred for 18 h at room temperature to give an orange precipitate ($UI_4(TMEDA)_2$). Excess HCl (4 M/1,4-dioxane, 0.26 mL, 1.0 mmol) was added to the suspension and the reaction mixture was stirred at room temperature for 4 h. Next, TMEDA (0.1226 g, 1.055 mmol) was added to the reaction mixture, which was stirred for 1 h to give a light green precipitate. The volatiles were then removed under reduced pressure to give $UCl_4(TMEDA)_2$ as a light green solid (0.118 g, 0.192 mmol, 91%). The $^1H$ NMR spectrum collected in toluene-$d_8$ was consistent with the data previously reported for $UCl_4(TMEDA)_2$ [27]. The $^1H$ NMR spectrum ($C_7D_8$ at 298 K) included the following peaks: δ 6.56 (broad singlet, 12H, $N(CH_3)_2$), −6.79 (broad singlet, 12H, $N(CH_3)_2$), −34.8 (s, 4H, $CH_2$), −60.6 (s, 4H, $CH_2$).

fc[NSi($^tBu$)Me$_2$]$_2$UI$_2$(THF) was synthesized by the following procedure: A 20-mL scintillation vial was charged with $[K_2(OEt_2)_2]$fc[NSi($^tBu$)Me$_2$]$_2$ (1.33 g, 1.99 mmol) and THF (20 mL). A second 20-mL scintillation vial was charged $UI_4(1,4\text{-dioxane})_2$ (1.84 g, 1.99 mmol) and THF (20 mL). Both solutions were cooled at −35° C. for at least 30 minutes. The cooled THF solution of $UI_4(1,4\text{-dioxane})_2$ was transferred to a 100-mL round bottom flask containing a stir bar, and the cooled THF solution of $[K_2(OEt_2)_2]$fc[NSi($^tBu$)Me$_2$]$_2$ was added to it dropwise with stirring. The reaction mixture was allowed to warm to room temperature while stirring for 1 h. The volatiles were removed under reduced pressure. The resulting brown solid was extracted into toluene (~40 mL) and filtered through a Celite-padded coarse-porosity flitted filter. The Celite plug was rinsed until the washings were colorless. The filtrate was collected and the volatiles were removed under reduced pressure. The extraction, filtration, and drying were repeated. The dried solid was scraped from the flask walls, transferred to a medium-porosity flitted filter, washed with about 40 mL hexane until the filtrate was nearly clear, and dried under reduced pressure, giving fc[NSi($^tBu$)Me$_2$]$_2$UI$_2$(THF) as a brown solid (1.21 g, 1.21 mmol, 61%). The $^1H$ NMR spectrum was consistent with the data previously reported for this complex [28]. The $^1H$ NMR spectrum ($C_6D_6$ at 298 K) included the following peaks: δ 56.6 (s, 12H, $SiCH_3$), 40.5 (s, 18H, SiC—$CH_3$), −20.3 (m, 4H, $C_5H_4$), −26.1 (s, 4H, THF-$CH_2$), −41.0 (m, 4H, $C_5H_4$), −74.0 (s, 4H, THF-$CH_2$).

$[(Me_3Si)_2N]_2U[\kappa^2\text{-}(C,N)\text{—}CH_2Si(Me)_2N(SiMe_3)]$ was synthesized using two procedures. The first procedure used $UI_4(1,4\text{-dioxane})_2$ as the precursor. The second procedure used $[UCl_4(1,4\text{-dioxane})]_2$ as the precursor. According to the first procedure, a 250-mL Schlenk flask was charged with a stir bar, $UI_4(1,4\text{-dioxane})_2$ (2.03 g, 2.20 mmol), K[N(SiMe$_3$)$_2$] (1.76 g, 8.81 mmol) and toluene (100 mL). The resulting yellow-orange suspension was transferred to a ventilation hood and heated in a 110° C. oil bath with stirring. After 15 h, the flask was cooled to room temperature, the stoppers were secured with electrical tape, and the flask was brought into an inert atmosphere drybox. The volatiles were then removed under reduced pressure to give a yellow residue, which was extracted into hexane (50 mL) and filtered through a Celite-padded medium-porosity fritted filter to remove salt byproducts. The Celite plug was washed with hexane (~10 mL) until the washings went colorless. The filtrate was collected and the volatiles were removed under reduced pressure to give $[(Me_3Si)_2N]_2U[\kappa^2\text{-}(C,N)\text{—}CH_2Si(Me)_2N(SiMe_3)]$ as a waxy yellow solid (1.10 g, 1.53 mmol, 70%). The $^1H$ NMR spectrum collected in $C_6D_6$ was consistent with the data previously reported for the compound [30]. The $^1H$ NMR spectrum ($C_6D_6$, 298 K) included the following peaks: δ 11.3 (s, 6H, $Si(CH_3)_2$), 9.7 (s, 9H, $Si(CH_3)_3$), −13.1 (s, 36H, $N[Si(CH_3)_3]_2$), −117.7 (s, 2H, U—$CH_2$).

The second procedure for synthesizing $[(Me_3Si)_2N]_2U[\kappa^2\text{-}(C,N)\text{—}CH_2Si(Me)_2N(SiMe_3)]$ used $[UCl_4(1,4\text{-dioxane})]_2$ as the precursor. A 100-mL round bottom flask was charged with a stir bar, [UCl$_4$(1,4-dioxane)]$_2$ (0.250 g, 0.267 mmol), Na[N(SiMe$_3$)$_2$] (0.462 g, 2.52 mmol) and toluene (45 mL). The flask was sealed and the resulting yellow suspension was stirred for 15 h at 110° C., using a thermocouple-equipped IKA stirring hotplate. The flask was then cooled to room temperature and the volatiles were removed under reduced pressure to give a yellow residue, which was extracted into hexane (25 mL) and filtered through Celite-padded medium-porosity fritted filter to remove salt byproducts. The Celite plug was washed with hexane (~10 mL) until the washings went colorless. The filtrate was collected and the volatiles were removed under reduced pressure to give [(Me$_3$Si)$_2$N]$_2$U[κ$^2$-(C,N)—CH$_2$Si(Me)$_2$N(SiMe$_3$)] as a waxy yellow solid (0.309 g, 0.431 mmol, 80%).

U(O-2,6-$^t$Bu$_2$C$_6$H$_3$)$_4$ was synthesized using two procedures. The first procedure used UI$_4$(1,4-dioxane)$_2$ as a precursor, and the second procedure used [UCl$_4$(1,4-dioxane)]$_2$ as the precursor. According to the first procedure, a 20-mL scintillation vial was charged with a stir bar, UI$_4$(1,4-dioxane)$_2$ (0.112 g, 0.121 mmol), K(O-2,6-$^t$Bu$_2$C$_6$H$_3$) (0.121 g, 0.495 mmol) and THF (5 mL). The resulting yellow suspension was stirred for 12 h at room temperature. The volatiles were removed under reduced pressure. The residue was dissolved in toluene (5 mL) and filtered through a Celite-padded coarse-porosity fritted filter. The orange filtrate was collected and the volatiles were removed under reduced pressure to give an orange solid residue. The residue was then extracted with hexane (5 mL) and filtered through a Celite-padded medium-porosity fritted filter. The filtrate was collected and the volatiles were removed under reduced pressure to give U(O-2,6-$^t$Bu$_2$C$_6$H$_3$)$_4$ as a dark yellow solid (0.082 g, 0.0774 mmol, 64%). The $^1$H NMR spectrum collected in C$_6$D$_6$ was consistent with the data previously reported for the compound [31, 32]. The $^1$H NMR spectrum (C$_6$D$_6$, 298 K) included the following peaks: δ 10.6 (d, 8H, m-Ar—CH), 8.4 (t, 4H, p-Ar—CH), −0.96 (br s, 72H, C—CH$_3$).

The second procedure for synthesizing U(O-2,6-$^t$Bu$_2$C$_6$H$_3$)$_4$ used [UCl$_4$(1,4-dioxane)]$_2$ as a precursor. According to this procedure, a 20-mL scintillation vial was charged with a stir bar, [UCl$_4$(1,4-dioxane)]$_2$ (0.0520 g, 0.0556 mmol), K[O-2,6-$^t$Bu$_2$C$_6$H$_3$] (0.118 g, 0.484 mmol) and toluene (10 mL). The reaction mixture was stirred for 15 h at 70° C., using a thermocouple-equipped IKA stirring hotplate. The resulting yellow suspension was filtered through a Celite-padded coarse-porosity fritted filter. The volatiles were removed under reduced pressure to give a yellow-orange crystalline solid, which was extracted with hexane (20 mL) and filtered through a Celite-padded medium-porosity fit. The filtrate was collected and the volatiles were removed under reduced pressure to give U(O-2,6-$^t$Bu$_2$C$_6$H$_3$)$_4$ as a dark yellow solid (0.0764 g, 0.0722 mmol, 65% yield).

(C$_5$Me$_5$)$_2$UI$_2$ was synthesized using UI$_4$(1,4-dioxane)$_2$ as a precursor. A 125-mL side-arm flask equipped with a magnetic stir bar was charged with K(C$_5$Me$_5$) (0.427 g, 2.45 mmol), UI$_4$(1,4-dioxane)$_2$ (1.13 g, 1.23 mmol), and toluene (35 mL). The reaction mixture was stirred for 18 h at 110° C. using a thermocouple-equipped IKA stirring hotplate. The resulting red-brown suspension was filtered through a Celite-padded coarse-porosity fritted filter, and the Celite plug was washed with toluene (20 mL) until the washings went colorless. Excess solvent was removed under reduced pressure. The red-brown residue was extracted into hexane (50 mL) and filtered through a Celite-padded coarse-porosity fritted filter, and the Celite plug was washed with hexane (50 mL) until the washings went colorless. The volatiles were removed under reduced pressure to give (C$_5$Me$_5$)$_2$UI$_2$ as waxy red-brown solid (0.605 g, 0.797 mmol, 65%). The $^1$H NMR spectrum collected in C$_6$D$_6$ was consistent with the data previously reported for the compound [34-36]. $^1$H NMR spectrum (C$_6$D$_6$, 298 K) included the following peak: δ 17.9 (s, 30H, C$_5$Me$_5$).

(C$_5$Me$_5$)$_2$UCl$_2$ was synthesized using [UCl$_4$(1,4-dioxane)]$_2$ as a precursor. A 125-mL side-arm flask equipped with a magnetic stir bar was charged with (C$_5$Me$_5$)MgCl(THF) (0.740 g, 2.77 mmol), [UCl$_4$(1,4-dioxane)]$_2$ (0.648 g, 0.692 mmol), and toluene (55 mL). To this solution was added 1,4-dioxane (2 mL), and the reaction mixture was capped and stirred for 15 h at 110° C. using a thermocouple-equipped IKA stifling hotplate. The resulting red suspension was filtered through a Celite-padded coarse-porosity fritted filter, and the Celite plug was washed with toluene (35 mL) until the washings went colorless. The volatiles were removed under reduced pressure. The red residue was extracted into hexane (50 mL) and filtered through a Celite-padded coarse-porosity fitted filter, and the Celite plug was washed with hexane (50 mL) until the washings went colorless. The filtrate was collected and the volatiles were removed under reduced pressure to give (C$_5$Me$_5$)$_2$UCl$_2$ as a red crystalline solid (0.560 g, 0.964 mmol, 70%). The $^1$H NMR spectrum collected in C$_6$D$_6$ was consistent with the data previously reported for the compound [37]. The $^1$H NMR spectrum (C$_6$D$_6$, 298 K) included the following peak: δ 13.5 (s, 30H, C$_5$Me$_5$).

UI$_3$(1,4-dioxane)$_{1.5}$ was synthesized using two procedures. The first was performed at room temperature, and the second was performed at 80° C. The first procedure began by charging a 20-mL scintillation vial with a stir bar, uranium turnings (2.50 g, 10.5 mmol), iodine (3.60 g, 14.2 mmol) and dioxane (10 mL). The reaction was vigorously stirred for 18 h at room temperature during which time the reaction mixture changed color from red to a blue-violet suspension. The reaction mixture was filtered through a medium-porosity fritted filter to collect the blue-violet solid. During the solid collection, care was taken to leave behind any unreacted uranium turnings. The solid was washed with diethyl ether (approximately 20 mL) and dried under reduced pressure to give UI$_3$(1,4-dioxane)$_{1.5}$ as a blue-violet solid (7.05 g, 9.38 mmol, 99%). Analysis calculated for C$_6$H$_{12}$I$_3$O$_3$U (mol. wt. 750.90): C, 9.60; H, 1.61; I, 50.70; U, 31.70; found: C, 11.06; H, 1.70; I, 50.4; U, 28.7.

The second procedure for synthesizing UI$_3$(1,4-dioxane)$_{1.5}$ began by charging a 50-mL thick-walled Schlenk tube sealed with a Teflon valve, and equipped with a magnetic stir bar, with uranium turnings (2.58 g, 10.8 mmol), iodine (3.71 g, 14.6 mmol) and 1,4-dioxane (12 mL). The reaction mixture was vigorously stirred in an 80° C. oil bath for 18 h. The flask was cooled to room temperature and brought into a drybox. The blue-violet suspension was concentrated to a thick sludge under reduced pressure, and Et$_2$O (10 mL) was added to precipitate a blue-violet solid. The solid was isolated by filtration through a coarse-porosity fitted filter, being careful to leave unreacted uranium turnings behind. The solid was dried under reduced pressure to give UI$_3$(1,4-dioxane)$_{1.5}$ as a blue-violet solid (5.77 g, 7.68 mmol, 79%).

UI$_3$(THF)$_4$ was synthesized using UI$_3$(1,4-dioxane)$_{1.5}$ as a precursor. A 20-mL scintillation vial was charged with a stir bar, UI$_3$(1,4-dioxane)$_{1.5}$ (0.346 g, 0.461 mmol) and THF (10 mL) to give a clear blue solution. The solution was stirred for 1 h at room temperature. The volatiles were then removed under reduced pressure to give UI$_3$(THF)$_4$ as a dark blue solid (0.410 g, 0.452 mmol, 98%). The $^1$H NMR spectrum collected in toluene-d$_8$ was consistent with the data previously reported for UI$_3$(THF)$_4$ [4]. The $^1$H NMR spectrum (toluene- $d_8$, 298 K) included the following peaks: δ 10.78 (broad singlet, 4H, THF-CH$_2$), 6.16 (broad singlet, 4H, THF-CH$_2$).

UI$_3$(pyridine)$_4$ was synthesized using UI$_3$(1,4-dioxane)$_{1.5}$ as a precursor. A 20-mL scintillation vial was charged with a stir bar, UI$_3$(1,4-dioxane)$_{1.5}$ (0.338 g, 0.450 mmol) and pyridine (10 mL) to give a blue-black solution. The solution was stirred for 4 h at room temperature. The volatiles were then removed under reduced pressure to give UI$_3$(py)$_4$ as a black microcrystalline solid (0.376 g, 0.402 mmol, 89%). The $^1$H NMR spectrum collected in C$_5$D$_6$ was consistent with the data previously reported for the compound [4]: $^1$H NMR (C$_6$D$_6$, 298 K): δ 18.17 (broad singlet, py-CH), 14.88 (broad singlet, py-CH), 11.46 (broad singlet, py-CH).

U(O-2,6-$^t$Bu$_2$C$_6$H$_3$)$_3$(THF) was synthesized using UI$_3$(1,4-dioxane)$_{1.5}$ as a precursor. A 20-mL scintillation vial was charged with a stir bar, UI$_3$(1,4-dioxane)$_{1.5}$ (0.240 g, 0.320 mmol) and THF (5 mL). With stirring, a THF (5 mL) solution of K(O-2,6-$^t$Bu$_2$C$_6$H$_3$) (0.234 g, 0.960 mmol) was added to the THF solution of UI$_3$(1,4-dioxane)$_{1.5}$ and the reaction mixture was stirred for 1 h at room temperature. The volatiles were then removed under reduced pressure. The resulting solid was then extracted into pentane (10 mL) and filtered through a Celite-padded pipette filter. The filtrate was collected and the volatiles were removed under reduced pressure to give U(O-2,6-$^t$Bu$_2$C$_6$H$_3$)$_3$(THF) as a brown solid (0.239 g, 0.258 mmol, 81%). The $^1$H NMR spectrum collected in C$_6$D$_6$ was consistent with the data previously reported for the compound [38]. The $^1$H NMR spectrum (C$_6$D$_6$, 298 K) included the following peaks: δ 16.07 (s, 6H, m-Ar—CH), 13.37 (s, 3H, p-Ar—CH), −1.61 (broad singlet, 54H, C—CH$_3$), −16.32 (broad singlet, 4H, THF-CH$_2$), −39.71 (broad singlet, 4H, THF-CR).

U(O-2,6-$^i$Pr$_2$C$_6$H$_3$)$_3$(THF) was synthesized using UI$_3$(1,4-dioxane)$_{1.5}$ as a precursor. A 20-mL scintillation vial was charged with a stir bar, UI$_3$(1,4-dioxane)$_{1.5}$ (0.324 g, 0.431 mmol) and THF (5 mL). A solution of K(O-2,6-$^i$Pr$_2$C$_6$H$_3$) (0.280 g, 1.29 mmol) in THF (5 mL) was added with stirring. The resulting reaction mixture was stirred for 1 h at room temperature. The reaction mixture was filtered through a Celite-padded coarse-porosity flitted filter and the Celite-plug was rinsed with THF (3×2 mL). The volatiles were removed under reduced pressure. The resulting solid was extracted into toluene (10 mL) and filtered through a Celite-padded pipette filter. The filtrate was collected and the volatiles were removed under reduced pressure to give U(O-2,6-$^i$Pr$_2$C$_6$H$_3$)$_3$(THF) as a brown solid (0.297 g, 0.352 mmol, 82%). The $^1$H NMR spectrum collected in C$_6$D$_6$ was consistent with the formation of the compound [38, 39]. The $^1$H NMR spectrum (C$_6$D$_6$, 298 K) included the following peaks: δ 11.23 (s, 6H, m-Ar—CR), 9.47 (s, 3H, p-Ar—CH), 1.06 (s, 6H, $^i$Pr—CH), −1.39 (s, 36H, $^i$Pr—CH$_3$), −3.31 (broad singlet, 4H, THF-CH$_2$), −6.06 (broad singlet, 4H, THF-CH$_2$).

U[N(SiMe$_3$)$_2$]$_3$ was synthesized using UI$_3$(1,4-dioxane)$_{1.5}$ as a precursor. A 125-mL side-arm flask was charged with a stir bar, UI$_3$(1,4-dioxane)$_{1.5}$ (1.00 g, 1.33 mmol), Na[N(SiMe$_3$)$_2$] (0.733 g, 4.00 mmol) and THF (45 mL). The resulting cloudy purple suspension was stirred for 1 h at room temperature. The solution was filtered through a Celite-padded medium-porosity hilted filter and the volatiles were removed under reduced pressure. The red-purple residue was extracted into pentane (50 mL) and filtered through a Celite-padded medium-porosity fritted filter. The filtrate was collected and the volatiles were removed under reduced pressure to give U[N(SiMe$_3$)$_2$]$_3$ as a red-purple powder (0.700 g, 0.970 mmol, 73%). The $^1$H NMR spectrum collected in C$_6$D$_6$ was consistent with the data previously reported for the compound [40, 41]. The $^1$H NMR spectrum (C$_6$D$_6$, 298 K) included the following peak: δ −11.4 (s, 54H, SiMe$_3$).

(C$_5$Me$_5$)$_2$UI(THF) was synthesized using UI$_3$(1,4-dioxane)$_{1.5}$ as a precursor. A 125-mL side-arm flask was charged with a stir bar, UI$_3$(1,4-dioxane)$_{1.5}$ (3.34 g, 4.45 mmol) and THF (80 mL). To the resulting dark blue solution was added K(C$_5$Me$_5$) (2.33 g, 13.3 mmol) as a solid. The solution immediately changed color to green. The reaction mixture was stirred for 36 h at room temperature and filtered through a Calite-padded medium-porosity fritted filter to remove salt byproducts. The Celite plug was washed with THF (15 mL) until the washings went colorless. The filtrate was collected and the volatiles were removed under reduced pressure. The resulting green-brown residue was extracted into toluene (60 mL) and filtered through a Celite-padded medium-porosity fritted filter. The filtrate was collected and THF (10 mL) was added to the solution. The volatiles were removed under reduced pressure to give a green-brown residue, which was extracted into hexane (75 mL) and filtered through a Calite-padded medium-porosity flitted filter. The Celite plug was then washed with THF (~10 mL) until the washings went colorless. The dark green filtrate was collected and the volatiles were removed under reduced pressure to give (C$_5$Me$_5$)$_2$UI(THF) as a dark green solid (2.35 g, 3.34 mmol, 75%). The $^1$H NMR spectrum collected in C$_6$D$_6$ was consistent with the data previously reported for the compound [42]. The $^1$H NMR spectrum (C$_6$D$_6$, 298 K) included the following peaks: δ −1.1 (broad singlet, 30H, C$_5$Me$_5$), −17.4 (broad singlet, 4H, THF-CH$_2$), −54.7 (broad singlet, 4H, THF-CH$_2$).

(C$_5$Me$_4$Et)$_2$UI(THF) was synthesized using UI$_3$(1,4-dioxane)$_{1.5}$ as a precursor. A 125-mL side-arm flask was charged with a stir bar, UI$_3$(1,4-dioxane)$_{1.5}$ (1.18 g, 1.57 mmol) and THF (75 mL). To the resulting dark blue solution was added K(C$_5$Me$_4$Et) (0.888 g, 4.71 mmol) as a solid. The solution immediately changed color to green. The reaction mixture was stirred for 15 h at room temperature and filtered through a Celite-padded medium-porosity fitted filter to remove salt byproducts. The Celite plug was washed with THF (15 mL) until the washings went colorless. The filtrate was collected and the volatiles were removed under reduced pressure. The resulting green-brown residue was extracted into toluene (30 mL) and filtered through a Celite-padded medium-porosity fitted filter. The Celite plug was washed with toluene (5 mL) until the washings went colorless. The filtrate was collected and THF (10 mL) was added to the solution. The volatiles were removed under reduced pressure to give a green-brown residue, which was extracted into hexane (35 mL) and filtered through a Celite-padded medium-porosity fitted filter. The Celite plug was then washed with THF (~5 mL) until the washings went colorless. The dark green filtrate was collected and the volatiles were removed under reduced pressure to give (C$_5$Me$_4$Et)$_2$UI(THF) as a dark green solid (0.775 g, 1.05 mmol, 67%). The $^1$H NMR spectrum collected in C$_6$D$_6$ was consistent with the data previously reported for compound [43]. The $^1$H NMR spectrum (C$_6$D$_6$, 298 K) included the following peaks: δ 16.85 (broad singlet, 6H, —CH$_2$CH$_3$), 0.09 (broad singlet, 4H, THF-CH$_2$), −0.963 (broad singlet, 4H, THF-CH$_2$), −3.51 (broad singlet, 12H, —CH$_3$), −4.01 (broad singlet, 12H, —CH$_3$), −18.21 (broad singlet, 4H, —CH$_2$CH$_3$).

U(=N$^t$Bu)$_2$(I)$_2$(O=PPh$_3$)$_2$ was synthesized using UI$_3$(1,4-dioxane)$_{1.5}$ as a precursor. A 20-mL scintillation vial was charged with UI$_3$(1,4-dioxane)$_{1.5}$ (0.208 g, 0.277 mmol) and THF (5 mL). A stir bar, $^t$BuNH$_2$ (0.138 g, 1.89 mmol), and I$_2$ (0.106 g, 0.416 mmol) were added to the vial, which was then stirred vigorously with frequent shaking for 10 min (giving U(=N$^t$Bu)$_2$(I)$_2$(THF)$_{2-3}$). The volatiles were removed under reduced pressure. The resulting solid was extracted into toluene (10 mL) and filtered through a Celite-filter-plugged pipette. The filtrate was collected and a solution of triphenylphosphine oxide ($Ph_3P=O$) (0.163 g, 0.585 mmol) in toluene (5 mL) was added with stirring. The solution was stored at room temperature for 15 h and $U(=N^tBu)_2(I)_2(O=PPh_3)_2$ deposited as bright red crystals (0.143 g, 0.120 mmol, 46%). The $^1H$ NMR spectrum collected in $CD_2Cl_2$ was consistent with the data previously reported for the compound [44]. The $^1H$ NMR spectrum ($CD_2Cl_2$, 298 K) included the following peaks: δ 8.38 (m, 12H, o-Ar—CH), 7.61 (m, 18H, m- and p-Ar—CH), 0.00 (s, 18H, C—$CH_2$).

An X-ray crystal structure of $UI_4(1,4\text{-dioxane})_2$ was determined from a crystal (0.10×0.08×0.08 mm) mounted in a nylon cryoloop using PARATONE-N oil under an argon gas flow. The data were collected on a BRUKER D8 APEX II charge-coupled-device (CCD) diffractometer with a KRYO-FLEX liquid nitrogen vapor cooling device. The instrument was equipped with a graphite monochromatized MoKα X-ray source (λ=0.71073 Å), with MONOCAP X-ray source optics. A hemisphere of data was collected using ω scans. Data collection and initial indexing and cell refinement were handled using APEX II software [APEXII 7.0, Bruker Analytical X-Ray Systems, Inc.: Madison, Wis., 2009]. Frame integration, including Lorentz-polarization corrections, and final cell parameter calculations were carried out using SAINT+software [SAINT+7.66a, Bruker Analytical X-Ray Systems, Inc.: Madison, Wis., 2009]. The data were corrected for absorption using the SADABS program [Sheldriek, G. M. SADABS, University of Göttingen: Göttingen, Germany, 2008]. Decay of reflection intensity was monitored by analysis of redundant frames. The structure was solved using Direct methods and difference Fourier techniques. Non-hydrogen atoms were refined anisotropically and hydrogen atoms were treated as idealized contributions. Structure solution, refinement, graphics, and creation of publication materials were performed using SHELXTL [SHELXTL 6.14, Bruker Analytical X-Ray Systems, Inc.: Madison, Wis., 2000]. Additional details regarding data collection are provided in the CIF file, which can be found at DOI: 10.1021/om200093q. The molecular structure of n ORTEP view of $UI_4(1,4\text{-dioxane})_2$ is shown in FIG. 1.

In summary, $UI_4(1,4\text{-dioxane})_2$ and $UI_3(1,4\text{-dioxane})_{1.5}$ are excellent precursors for a wide variety of uranium(IV) and uranium(III) compounds and are easily prepared on a large scale. $UI_4(1,4\text{-dioxane})_2$ was used to prepare $[UCl_4(1,4\text{-dioxane})]_2$, which has proved to be a synthetic alternative to $UCl_4$. These uranium compounds are expected to become important reagents in synthetic actinide chemistry and to allow progress in uranium materials science and nuclear fuel cycle research.

All documents (i.e. references) cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition, of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

References

[1] Morss et al. editors, "The Chemistry of Actinide and Transactinide Elements, $3^{rd}$ ed.," Springer: The Netherlands, 2006.
[2] Morss et al., editors, "The Chemistry of Actinide and Transactinide Elements, $4^{th}$ ed.," Springer: The Netherlands, 2011, vol. 6.
[3] Clark et al., Inorg. Chem., (1989) vol. 28, pp. 1771-1773.
[4] Avens et al., Inorg. Chem., (1994) vol. 33, pp. 2248-2256.
[5] Hermann et al., Inorg Chem., (1957) vol. 5, pp. 143-145.
[6] Uhlemann et al., (1963) vol. 3, pp. 431-432.
[7] Wilson, Syn. Inorg. Met.-Org. Chem., (1973), vol. 3, pp. 381-385.
[8] Khan et al., Inorg., Synth., (1982), vol. 21, pp. 187-190.
[9] Kiplinger et al., Organometallics, (2002), vol. 21, pp. 5978-5982.
[10] Schleid et al., Less-Common Met., (1987), vol. 132, pp. 69-77.
[11] Brown et al., J. Chem. Soc. Dalton Trans., (1972), pp. 1757-1762.
[12] Van de Weghe et al., Inorg. Chim. Acta, (1994), vol. 222, pp. 91-94.
[13] Cloke et al., J. Am. Chem. Soc., (2002), vol. 124, pp. 9352-9353.
[14] Evans et al., Inorg. Chem., (2005), vol. 44, pp. 3993-4000.
[15] Larch et al., Chem. Commun., (2008), pp. 82-84.
[16] Du Preez et al., Inorg. Chim. Acta, (1987), vol. 129, pp. 289-296.
[17] Du Preez et al., Inorg. Chim. Acta, (1987), vol. 134, pp. 303-308.
[18] Avens et al., Inorg. Chem., (1996), vol. 35, pp. 537-539.
[19] Berthet et al., Inorg. Chem., (2005), vol. 44, pp. 1142-1146.
[20] Enriquez et al., Inorg. Chem., (2005), vol. 44, pp. 7403-7413.
[21] Carmichael et. al., Inorg. Chem., (2008), vol. 47, pp. 8577-8579.
[22] Schnaars et al., Dalton Trans., (2008), pp. 6121-6126.
[23] Cantat et al., Chem. Commun., (2010), vol. 46, pp. 919-921.
[24] Collin et al., J. Organomet. Chem., (1993), vol. 463, pp. 103-107.
[25] Schnaars et al., Dalton Trans., (2009), pp. 3681-3587.
[26] Camboli et al., Rev. Roam. Chim., (1976), vol. 21, pp. 1479-1485.
[27] Edwards et al., J. Alloys Compd., (1994), 213, pp. 11-14.
[28] Monreal et al., Organometallics, (2008), vol. 27, pp. 1702-1706.
[29] Simpson et al., Inorg. Chem., (1981), vol. 20, pp. 2991-2995.
[30] Dormond et al., J. Organomet. Chem., (1985), vol. 288, pp. C1-C5.
[31] Van der Sluys et al., Polyhedron, (1989), vol. 8, pp. 1247-1249.
[32] Berg et al., J. Am. Chem. Soc. (1992), vol. 114, pp. 10811-10821.
[33] McKee et al., Inorg. Chem., (1998), vol. 37, pp, 4040-4045.
[34] Maynadie et al., J. Am. Chem. Soc., (2006), vol. 128, pp, 1082-1083.
[35] Maynadie et al., Organometallics, (2006), vol. 25, pp. 5603-5611.
[36] Graves et al., Organometallics, (2008), vol. 27, pp. 5371-5378.
[37] Fagan et al., J. Am. Chem. Soc., (1981), vol. 103, pp. 6650-6667.

[38] Van der Sluys et al., J. Am. Chem. Soc., (1988), vol. 110, pp. 5924-5925,
[39] Clark, et al., J. Alloys Compd., (1992), vol. 180, pp. 303-315.
[40] Andersen, Inorg. Chem., (1979), vol. 18, pp. 1507-1509.
[41] Steward et al., Polyhedron, (1998), vol. 17, pp. 953-958.
[42] Avens et al., Organometallics, (2000), vol. 19, pp. 451-457.
[43] Schelter et al., Angew. Chem., Int. Ed., (2008), vol. 47, pp. 2993-2996.
[44] Hayton et al., J. Am. Chem. Soc., (2006), vol. 128, pp. 10549-10559.
[45] Monreal et al., Inorg. Chem., (2007), vol. 46, pp, 7226-7228.
[46] Evans et al., J. Am. Chem. Sac., (2004), vol. 126, pp. 14533-14547.
[47] Geerts et al., Inorg. Chem., (1986), vol. 25, pp. 1803-1805.

What is claimed is:

1. A composition selected from the group consisting of $UI_4(1,4\text{-dioxane})_2$, $[UCl_4(1,4\text{-dioxane})]_2$, and $UI_3(1,4\text{-dioxane})_{1.5}$.

2. A process for synthesizing $UI_x(1,4\text{-dioxane})_y$, comprising:
    reacting suitable amount of elemental uranium with a suitable amount of iodine ($I_2$) dissolved in 1,4-dioxane to form a suspension comprising a solid,
    isolating the solid from the suspension, and
    drying the solid under reduced pressure, thereby synthesizing $UI_x(1,4\text{-dioxane})_y$, wherein x is 3 and y is 1.5, or wherein x is 4 and y is 2.

3. A process for synthesizing a molecular compound of uranium, comprising:
    providing a solution of $UI_x(1,4\text{-dioxane})_y$ wherein x is 3 and y is 1.5, or wherein x is 4 and y is 2, and
    reacting the solution of $UI_x(1,4\text{-dioxane})_y$ under suitable conditions to form the molecular compound of uranium.

4. The process of claim 3, wherein a solution of $UI_3(1,4\text{-dioxane})_{1.5}$ is reacted under suitable conditions to form a molecular compound selected from $UI_3(\text{tetrahydrofuran})_4$, $UI_3(\text{pyridine})_4$, $U(OAryl)_3(\text{tetrahydrofuran})$, $U(N(SiMe_3)_2)_3$, $(C_5Me_4R)_2U(I)(\text{tetrahydrofuran})$ wherein R is selected from $CH_3$- and $CH_3CH_2$, and $U(\!\!=\!\!N^tBu)_2(I)_2(O\!\!=\!\!PPh_3)_2)$.

5. The process of claim 3, wherein a solution of $UI_4(1,4\text{-dioxane})_2$ is reacted under suitable conditions to form a molecular compound selected from $UI_4(\text{diethyl ether})_2$, $[UCl_4(1,4\text{-dioxane})]_2$, $UCl_4(N,N,N',N'\text{-tetramethylethylenediamine})_2$, $fc[NSi(^tBu)Me_2]_2UI_2(THF)$, $[(Me_3Si)_2N]_2U[\kappa^2\text{-}(C,N)\text{---}CH_2Si(Me)_2N(SiMe_3)]$, $U(OAryl)_4$, and $(C_5Me_5)_2UI_2$.

* * * * *